United States Patent [19]

Minami et al.

[11] Patent Number: 4,906,648
[45] Date of Patent: Mar. 6, 1990

[54] INDUSTRIAL ANTIFUNGAL COMPOSITION

[75] Inventors: Toshikazu Minami; Kosaku Matsumoto, both of Oosaka; Hiroshi Nanto, Kanagawa, all of Japan

[73] Assignees: SDS Biotech Kabushiki Kaisha, Tokyo; Shinto Paint Co., Ltd., Hyogo, both of Japan

[21] Appl. No.: 183,018

[22] Filed: Apr. 18, 1988

[30] Foreign Application Priority Data

Apr. 17, 1987 [JP] Japan ................... 62-93337

[51] Int. Cl.$^4$ ...................... A01N 43/52; A01N 43/78
[52] U.S. Cl. .................... 514/365; 514/395; 514/525
[58] Field of Search ......... 514/365, 395, 525

[56] References Cited

U.S. PATENT DOCUMENTS 3,331,735  7/1967  Battershell et al. ............... 514/525

FOREIGN PATENT DOCUMENTS 882357  11/1961  United Kingdom .

Primary Examiner—Leonard Schenkman
Attorney, Agent, or Firm—Wenderoth, Lind & Ponack

[57] ABSTRACT

Industrial antifungal compositions of the present invention contain as active ingredients both the compounds represented by the general formula (I) and the compounds represented by the general formula (II), said general formulas being mentioned below. By virtue of using two kinds of compounds mentioned above in combination in the compositions, antifungal properties of the present composition sharply augment and hence said compositions are found to have excellent antifungal properties as well as excellent antifungal activities against a wide variety of species of fungi and, moreover, the present compositions are excellent in safety and free from tending to accumulation.

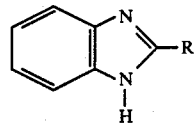

(I)

wherein R represents methoxycarbonylamino, ethoxycarbonylamino or 4-thiazolyl.

3 Claims, No Drawings

INDUSTRIAL ANTIFUNGAL COMPOSITION

FIELD OF THE INVENTION

This invention relates to industrial antifungal compositions, more particularly to industrial antifungal compositions having excellent antifungal activities and which are excellent in safety.

BACKGROUND OF THE INVENTION

Heretofore, halogenated phenol compounds or organotin compounds have frequently been used as active ingredients of industrial antifungal agents. However, in light of the fact that these compounds are strong in acute toxicity as well as in chronic toxicity and also relatively hard to decompose, there is an ever-present fear for a secondary environmental pollution caused by accumulation of said compounds in the antifungal agents containing the same. Accordingly, these compounds have now come to be unadaptable for use as active ingredients in the industrial antifungal agents in future.

On that account, antifungal agents which are higher by far in safety have come to be developed enthusiastically. To mention one example of the development, there are provided such compounds as developed, for example, 2-benzimidazole carbamic acid esters, 2-(4-thiazolyl)benzimidazole, etc. However, as revealed from MIC(aluminum inhibition concentrations) of these benzimidazole compounds against various species of fungi, they are greatly devoid of suitability for use as active ingredients of fungicides to be applied to industrial materials and products which are usually exposed to risk of contamination with a wide variety of species of fungi, though these compounds show their usefulness when used in fungicidal agents for agricultural and horticultural application wherein the contamination of plants with relatively limited species of fungi becomes a problem. For this reason, there has been made an attempt to broaden the fungicidal spectrum or augment fungi resistance of the antifungal agents by combining a plurality of antifungal agents different in kind. However, the fact is that the effect as obtained thereby is usually limited only that of one of the antifungal agents or to one of the expected addition effects at most.

OBJECT OF THE INVENTION

The present invention is intended to solve such problems associated with the prior art as mentioned above, and an object of the invention is to provide industrial antifungal compositions which have excellent antifungal activities as well as excellent broad spectrum against a wide variety of species of fungi and, moreover, which are excellent in safety and free from tending to accumulation and therefore which are possible to minimize a usage amount.

The present invention conducted extensive researches with the view of solving such problems as mentioned above and have eventually accomplished the present invention on the basis of their finding that a composition comprising a combination of a compound represented by the formula (I) and a compound represented by the formula (II), both formulas will be mentioned later, is sharply augmented in antifungal activities as compared with the case where these compounds are used singly.

SUMMARY OF THE INVENTION

The industrial antifungal composition of the present invention is characterized by containing as its active ingredients at least one compound represented by the general formula (I)

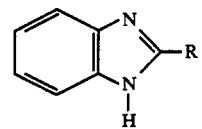

(I)

wherein R represents methoxycarbonylamino, ethoxycarbonylamino or 4-thiazolyl, and at least one compound represented by the general formula (II)

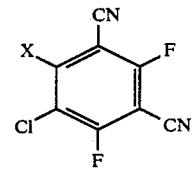

(II)

wherein X represents halogen or lower alkoxy of 1 to 4 carbon atoms.

Since the industrial antifungal composition of the present invention contains as its active ingredients both the compound of the formula (I) and the compound of (II) as mentioned above, which compounds must be used in combination, antifungal activities of the composition is sharply augmented and, consequently, the composition comes to have excellent antifungal activities against a wide variety of species of fungi, and comes to have excellent in safety and free from tending to accumulation and therefore comes to minimize a usage amount.

DETAILED DESCRIPTION OF THE INVENTION

The industrial antifungal compositions of the present invention are illustrated below in detail.

Examples of the compounds of the formula (I) used in the industrial antifungal compositions of the present invention include methyl 2-benzimidazole carbamate, ethyl 2-benzimidazole carbamate, 2-(4-thiazolyl)benzimidazole.

In this connection, these benzimidazole type compounds as illustrated above are known to be high in safety and free from tending to accumulation. As mentioned previously, however, they have selectivity to fungicidal spectrum and are of no practical use when they are used singly.

The compounds of the formula (II) used in the industrial antifungal compositions of the present invention includes 5-chloro-2,4,6-trifluoroisophthalonitrile, 5-chloro-2,4-difluoro-6-methoxyisophthalonitrile, 4-n-butoxy-5-chloro-2,6-difluoroisophthalonitrile, etc.

These isophthalonitrile compounds exemplified capable of markedly minimizing the amount used thereof by synergistic effect obtained by the use of the aforementioned imidazole type compounds in combination therewith, and thus in accordance with the present invention it is possible to provide industrial antifungal compositions which are harmless in view of a utility standpoint.

The proportion of the compounds of the formula (I) to the compounds of the formula (II) used in the industrial antifungal compositions of the present invention may be varied. However, the benzimidazole type compounds of the formula (I) is preferably present in the compositions in an amount of 10-90% by weight, more preferably 30-70% by weight, based on the sum total weight of the benzimidazole type compounds of the formula (I) and the isophthalonitrile compounds of the formula (II) because the synergistic effect of these two compounds is markedly exhibited in particular.

According to the purpose for which they are used, the antifungal compositions of the present invention are applicable, as they are, directly to the objects to which they are applied, or they are applicable thereto after having been formed into such various formulations, for example, as oil type formulations prepared by dissolving the present compositions in such liquids as alcohols, glycols, alkyl ethers of glycol and aromatics; emulsion type formulation prepared by adding to said oil type formulations nonioic surfactants, such as polyoxyethylene alkyl ethers, polyoxyethylene alkylaryl ether, polyoxyethylene alkyl esters, sorbitan fatty acid esters, polyoxyethylene sorbitan fatty acid esters, etc. and anionic surfactants, such as sulfate ester salts of polyethylene glycol ether, sulfanates of fatty acid ester, phosphates ester salts of polyethlene glycol ether phosphats-aqueous suspensions (flowable formulations) prepared by rendering the present antifungal compositions hydrophilic on the surface thereof in water with nonionic surfactants, such as polyoxyethylene alkylphenyl ethers, polyoxyethylene alkyl ethers, polyoxyethylene styrylphenyl ethers, etc.; dispersing the thus treated compositions with anionic surfactants, such as dialkyl succinates, condensates of naphthalenesulfonic acid with formalin, polyoxyethylene alkylallylethers, etc., and adding to the thus dispersed compositions such protective colloid as guar gum, gum arabic, tragacanth gum, xanthan gum, alkali salts of carboxymethyl cellulose, ammonium arginate, polyvinyl alcohol, polyvinyl pyrrolidone, sodium polyacrylate, polyacrylic acid amide, etc., and thickeners; fine particulate formulations prepared by mixing the present compositions with clay, talc, calcium carbonate, amorphous silicon dioxide, aluminum silicate, etc., wettable powders prepared by adding to said fine particulate formulations such nonionic surfactants as polyoxyethylene alkyl ethers, polyoxyethylene alkylaryl ethers, polyoxyethylene alkyl esters, sorbitan fatty acid esters, and such anionic surfactants as sulfate ester salts of polyethylene glycol ether, sulfonates of fatty acid esters, phosphate ester salts of polyethylene glycol ether; and other granular and past formulations.

Furthremore, the antifungal compositions of the present invention can also be used in admixture with other antifungal compounds such as N-fluorodichloromethylthio phthalimide, o-phenylphenol, bis(tributyltin)oxide, 2-(thiocyanomethylthio) benzthiazole, N,N-dimethyl-N'-phenyl(N'-fluorodichloromethylthio)-phthalimide, Al-N-nitroso-N-cyclohexyl hydroxylamine, Zn-2-pyridinethiol-1-oxide, diiodomethyl-p-torylsulfone, 2,4,4'-trichloro-2'-hydroxydiphenyl ether, etc.; bactericicides such as 1,2-benzisothiazoline-3-one, methylene bisthiocyanate, 2-methy-4-chloroisothiazoline-3-one, tetrahydro-3,5-dimethyl-2H-1,3,5-thiadiazine-2-thione, bisbromoacetoxyethane, 2-bromo-2-nitrobutane-1,3-diol, 2-bromo-2-bromomethylglutaronitrile, 2,2-dibromo-3-nitrilopropionamide, bis(tribromomethyl) sulfone, etc.; and insecticides such as O,O-dimethyl-O-(3-methyl-1,4-nitrophenyl) phosphorothioate (Fenitrothione), O,O-dimethyl-O-(3-methyl-4-methylthiophenyl)phosphorothioate (Fenthione), O-(2,2-dichlorovinyl)-O,O-dimethyl phosphate (Dichlorvor), O,O-dimethyl-O-(2-isopropyl-4-methyl-6-pyrimidinyl) phosphorothioate (Diazinone),O-2,4-dichlorophenyl-O-ethyl-5-propyl phosphorodithoate (Frothiofos), (E)-O-2-isopropoxycarbonyl-1,1-,methylvinyl-O-methyl-N-ethyl phosphoramidothioate (Propilanphos),O,O-dimethyl-O-(3,5,6-trichloro-2-pyridyl)-phosphorothioate (Chlopyrifod-methyl), etc.

The antifungal compositions of the present invention are applicable to various industrial materials and products, for example, paints, wating colors adhesives, fibers, wood and bamboo products, leather products, paper products, electronic parts, wall decorative materials, resin molded articles, etc.

The following examples and test examples of the present invention are set forth, by way of illustration but not of limitation. In these examples, percentages and parts are by weight unless specified otherwise, and names of the compounds used therein are abbreviated as in the following.

| Compounds of the general formula (I) | |
|---|---|
| Methyl 2-benzimidazole carbamate: | BICM |
| Ethyl 2-benzimidazole carbamate: | BICE |
| 2-(4-Thiazolyl)benzimidazole: | TBZ |
| Compounds of the general formula (II) | |
| 5-Chloro-2,4,6-trifluoroiso-phthalonitrile: | FPN |
| 5-Chloro-2,4-difluoro-6-methoxy-isophthalonitrile: | MPN |
| Other known antifungal compounds | |
| 2-Octyl 4-chloroiso thinazoline-3-one | OCIT |
| 2,4,6-trichlorophenol | TCP |

EXAMPLE 1

(wettable powder)

A wettable powder was prepared by homogeneously mixing together 5% TBZ, 5% FPN, 5% polyoxyethylene octylphenyl ether sulfate and 85% clay, followed by pulverization.

EXAMPLE 2

(flowable)

A flowable formulation was prepared by mixing together 3% BICM, 7% MPN, 1.5% polyoxyethylene stylylphenyl ether, 1% dioctyl sulfosuccinate, 4% white carbon, 0.15% xanthan gum and 83.55% water, followed by passing through a wet grinder.

EXAMPLE 3

(flowable)

A flowable formulation was prepared by mixing together 7% BICE, 3% MPN, 1.5% polyoxyethylene estylylphenyl ether, 1% dioctyl sulfosuccinate, 4% white carbon, 0.15% xanthan gum and 83.35% water, followed by passing through a wet grinder.

CONTROL EXAMPLES

There were prepared formulations containing 10% each of BICM, BICE, TBZ, FPN, and MPN above as an effective ingredient. Further, formulations containing 5% of one of the compounds of the general formula (I) or (II) in combination with 5% of OCIT or TCP were prepared. The formulations as prepared were used as control examples.

Test Examples 1 (fungus resistance of emulsion paint)

A vinyl acetate-acrylic type emulsion paint (ENVI ® #60, a product of Shinto Paint Company, Limited) incorporated with a specified amount of the antifungal agent was uniformly coated on qualitative test filter paper in the same weight as of said filter paper and then dried to prepare a specimen. Thereafter, antifungal performance of the thus incorporated antifungal composition was evaluated in accordance with the test method of paint as described in "Methods of Test for Fungus Resistance" stipulated in JIS Z 2911. In the test conducted, there were used as the test strains the strains (Penicillium sp., Cladosporium sp.) which had actually grown on the surface of the specimen in addition to the strains specified in the aforesaid JIS. The results obtained are shown in Table 1. In the table, the degree of fungus growth was determined according to the following ratings.

| | |
|---|---|
| (−) | No fungus growth is observed at all on the specimen. |
| (+) | The area of the specimen on which fungus have grown does not exceed 1/10 of the total area of said specimen. |
| (++) | The area of the specimen on which fungus have grown is 1/10 to ½ of the total area of said specimen. |
| (+++) | The area of the specimen on which fungus have grown exceeds ½ of the total area of said specimen. |

In the test results obtained in Test Examples 2 and 3, respectively, the same ratings as above were adopted, as well.

TABLE 1

| Composition tested | Amount added (%) | Degree of fungus growth |
|---|---|---|
| No active ingredient contained | 0 | +++ |
| Composition of Example 1 | 0.25 | + |
|  | 0.5 | − |
| TBZ 5% | 1 | − |
| FPN 5% | 2 | − |
| Control Example 1 | 0.25 | +++ |
| TBZ 10% (wettable powder) | 0.5 | +++ |
|  | 1 | +++ |
|  | 2 | + |
| Control Example 2 | 0.25 | +++ |
| FPN 10% (wettable powder) | 0.5 | ++ |
|  | 1 | − |
|  | 2 | − |
| Control Example 3 | 0.25 | +++ |
| TBZ 5% | 0.5 | ++ |
| OCIT 5% | 1.0 | ++ |
|  | 2.0 | + |
| Control Example 4 | 0.25 | +++ |
| TBZ 5% | 0.5 | ++ |
| TCP 5% | 1.0 | + |
|  | 2.0 | + |
| Control Example 5 | 0.25 | +++ |
| FPN 5% | 0.5 | ++ |
| OCIT 5% | 1.0 | + |
|  | 2.0 | + |
| Control Example 6 | 0.25 | +++ |
| FPN 5% | 0.5 | ++ |
|  | 1.0 | + |

TABLE 1-continued

| Composition tested | Amount added (%) | Degree of fungus growth |
|---|---|---|
| TCO 5% | 2.0 | − |

As is clear from the results shown in Table 1, a marked antifungal effect of the present compositions was observed in comparison with the cases where the active ingredients were used alone or in combination with an antifungal compound other than those contemplated herein.

Test Example 2 (fungus resistance of wood)

As sapwood of Scotch pine (2 cm width × 5 cm length × 0.5 cm thick) was dipped for 30 seconds in a bath of the active ingredient diluted to a specified concentration, followed by air drying. This specimen was placed on a potato dextrose agar plate, and 1 ml of a mixed fungus spore flowable formulatlion was sprayed over the specimen, followed by culturing at 28° C. for 14 days. The test strains used were *Chaetominum globosum*, *Tricoderma viride*, *Penicillium funiculosum* and a wild strain (Fusarium sp.) actually grown on the Scotch pine. The results obtained are shown in Table 2.

TABLE 2

| Composition tested | Concentration of bath (%) | Degree of fungus growth |
|---|---|---|
| No active ingredient contained | 0 | +++ |
| Composition of Example 2 | 0.5 | + |
|  | 1 | − |
| BICM 3% | 2 | − |
| MPN 7% | 4 | − |
| Control Example 7 | 0.5 | +++ |
|  | 1 | +++ |
| BICM 10% (suspension) | 2 | +++ |
|  | 4 | + |
| Control Example 8 | 0.5 | +++ |
|  | 1 | ++ |
| MPN 10% (suspension) | 2 | + |
|  | 4 | + |

As is clear from the results shown in Table 2, a marked antifungal effect of the present composition was observed in comparison with the cases where the active ingredients were used singly as shown in Control Examples.

Test Example 3 (fungus resistance of sized cotton cloth)

A mixture comprising 5 parts wheat starch, 2.5 parts PVA, 0.5 part Maconol ® H (a softener, a product of Matsumoto Fats & Oils Co. Ltd.) and 92 parts water was warmed to prepare a sizing solution. The sizing solution was incorporated with a specified amount of the active ingredient, and thereafter broad cotton cloth was dipped with said sizing solution of the same weight as that of said cotton cloth and then dried. Thereafter, antifungal performance of the active ingredient thus incorporated was evaluated on the basis of the Textile Product Test Method (wet process) as stipulated in "Methods of Test for Fungus Resistance" of JIS Z 2911. In the test, there were used as the test strains the strains (Cladosproium sp., Alternaria sp.) actually grown on the cotton cloth in addition to the strains as specified in said JIS. The results obtained are shown in Table 3.

TABLE 3

| Composition tested | Amount added (%) | Degree of fungus growth |
| --- | --- | --- |
| No active ingredient contained | 0 | +++ |
| Present composition of Example 3 | 0.05 | + |
|  | 0.1 | − |
| BICE 5% | 0.2 | − |
| MPN 5% | 0.4 | − |
| Control Example 9 | 0.05 | +++ |
|  | 0.1 | +++ |
| BICE 10% | 0.2 | ++ |
| (flowable formulation) | 0.4 | + |
| Control Example 10 | 0.05 | +++ |
|  | 0.1 | ++ |
| MPN 10% | 0.2 | ++ |
| (flowable formulation) | 0.4 | − |

As is clear from the results shown in Table 3, a marked antifungal effect of the present composition was observed in comparison with the cases where the active ingredients were used singly as shown in Control Examples.

The compositions of the present invention, as can be evidenced by the foregoing test examples, exhibit a markedly improved effectiveness in comparison with the cases where the compositions used contain the active ingredients alone, or in combination with an antifungal compound other than those contemplated herein, and that they are quite suitable as antifungal agents for use in various industrial materials and products.

What is claimed is:

1. An industrial antifungal composition comprising at least one compound represented by the formula (I)

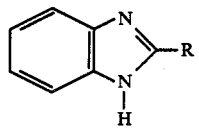

wherein R represents methoxycarbonylamino, ethoxycarbonylamino or 4-thiazolyl, and at least one compound represented by the formula (II)

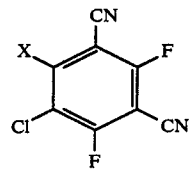

wherein X represents halogen or lower alkoxy of 1 to 4 carbon atoms,
the compound represented by formula (I) being present in an amount of 50 to 305 by weight and the compound represented by formula (II) being present in an amount of 50 to 70% by weight based on the total weight of the compounds represented by formulas (I) and (II).

2. The composition as claimed in claim 1 wherein the compound represented by formula (I) is methyl 2-benzimidazole carbamate, or 2-(4-thiazolyl) benzimidazole.

3. The composition as claimed in claim 1 wherein the compound represented by formula (II) is 5-chloro-2,4,6-trifluoroisophthalonitrile, 5-chloro-2,4-difluoro-6-methoxyisophthalonitrile or 4-n-butoxy-5-chloro-2,6-difluoroisophthalonitrile.

* * * * *